(12) United States Patent
Ehlers et al.

(10) Patent No.: US 10,058,243 B2
(45) Date of Patent: Aug. 28, 2018

(54) CLINIC EVALUATION VIA OUTER RETINAL LAYER ASSESSMENT

(71) Applicant: THE CLEVELAND CLINIC FOUNDATION, Cleveland, OH (US)

(72) Inventors: Justis P. Ehlers, Shaker Hts., OH (US); Sunil Srivastava, Shaker Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 162 days.

(21) Appl. No.: 15/053,506

(22) Filed: Feb. 25, 2016

(65) Prior Publication Data
US 2016/0242639 A1    Aug. 25, 2016

Related U.S. Application Data

(60) Provisional application No. 62/120,579, filed on Feb. 25, 2015.

(51) Int. Cl.
*A61B 3/10* (2006.01)
*G06T 7/00* (2017.01)

(52) U.S. Cl.
CPC ............ *A61B 3/102* (2013.01); *G06T 7/0012* (2013.01); *G06T 2207/10101* (2013.01); *G06T 2207/30041* (2013.01)

(58) Field of Classification Search
CPC .............................. A61B 3/0025; A61B 3/102
USPC ......................................................... 351/246
See application file for complete search history.

(56) References Cited

U.S. PATENT DOCUMENTS

2007/0115481 A1   5/2007  Toth et al.
2012/0194783 A1   8/2012  Wei et al.

FOREIGN PATENT DOCUMENTS

EP    2742856 A1    6/2014
EP    2759254 A1    7/2014
WO    2007084748 A2  7/2007
WO    2013148687 A2  10/2013

OTHER PUBLICATIONS

Ehlers, Justis P., et al. "Intrasurgical dynamics of macular hole surgery: an assessment of surgery-induced ultrastructural alterations with intraoperative optical coherence tomography." Retina 34.2 (2014): 213-221.

(Continued)

*Primary Examiner* — Jack Dinh
(74) *Attorney, Agent, or Firm* — Tarolli, Sundheim, Covell & Tummino LLP

(57) ABSTRACT

Systems and methods are provided for evaluating an eye of a patient from a set of OCT data. A layer segmentation component is configured to identify and segment a plurality of retinal layers within the set of OCT data. The plurality of layers include a layer of interest. A mapping component is configured to generate at least one of an en face representation of the layer of interest and a three-dimensional reconstruction of the layer of interest from the segmented plurality of layers. A parameter generator is configured to derive at least one parameter, representing a thickness of the layer of interest, from the at least one of the en face representation of the layer of interest and the three-dimensional reconstruction of the layer of interest. A user interface is configured to provide the determined at least one parameter to a display.

18 Claims, 3 Drawing Sheets

(56) References Cited

OTHER PUBLICATIONS

Ehlers, Justis P., et al. "Factors Associated With Persistent Subfoveal Fluid and Complete Macular Hole Closure in the PIONEER StudyPersistent Subfoveal Fluid Following MH Surgery." Investigative ophthalmology & visual science 56.2 (2015): 1141-1146.

Freund, K. B., S. A. Shah, and V. P. Shah. "Correlation of transient vision loss with outer retinal disruption following intravitreal ocriplasmin." Eye 27.6 (2013): 773.

Hibi, Nobuaki, et al. "Relationship Between Retinal Layer Thickness and Focal Macular Electroretinogram Components After Epiretinal Membrane SurgeryRetinal Layer Thickness and FMERGs After ERM Surgery." Investigative ophthalmology & visual science 54.12 (2013): 7207-7214.

Itoh, Yuji, et al. "Assessment of retinal alterations after intravitreal ocriplasmin with spectral-domain optical coherence tomography." Ophthalmology 121.12 (2014): 2506-2507.

Ray, Robin, et al. "Intraoperative microscope-mounted spectral domain optical coherence tomography for evaluation of retinal anatomy during macular surgery." Ophthalmology 118.11 (2011): 2212-2217.

Abramoff, Michael D., Mona K. Garvin, and Milan Sonka. "Retinal imaging and image analysis." IEEE reviews in biomedical engineering 3 (2010): 169-208.

Wojtkowski, Maciej. "High-speed optical coherence tomography: basics and applications." Applied Optics 49.16 (2010): D30-D61.

PCT International Search Report and Written Opinion for PCT/US2016/019553, dated Jun. 3, 2016, pp. 1-13.

CLINIC EVALUATION VIA OUTER RETINAL LAYER ASSESSMENT

RELATED APPLICATIONS

The present application claims priority to U.S. Provisional Patent Application Ser. No. 62/120,579 filed Feb. 25, 2015 entitled OPTICAL COHERENCE TOMOGRAPHY IMAGING BIOMARKERS AND INTEGRATIVE PATTERN ANALYSIS, the entire contents of which being incorporated herein by reference in its entirety for all purposes.

GOVERNMENT FUNDING

This invention was made with government support under EY022947 awarded by the National Institutes of Health. The government has certain rights in the invention.

TECHNICAL FIELD

The present invention relates generally to the field of medical imaging, and more particularly to clinic evaluation of the retina from imaging and evaluation of the outer layers of the retina.

BACKGROUND OF THE INVENTION

Optical coherence tomography (OCT) is an optical signal acquisition and processing method that captures micrometer-resolution, three-dimensional images from within optical scattering media, such as biological tissue. Optical coherence tomography is an interferometric technique, typically employing near-infrared light. The use of relatively long wavelength light allows it to penetrate into the scattering medium. Depending on the properties of the light source, optical coherence tomography has achieved sub-micrometer resolution. Optical coherence tomography systems are employed in diverse applications, including art conservation and diagnostic medicine, notably in ophthalmology where it can be used to obtain detailed images from within the retina and other ophthalmic tissues (e.g., cornea).

SUMMARY OF THE INVENTION

In accordance with an aspect of the present invention, a system is provided for evaluating an eye of a patient from a set of OCT data. The system includes a processor and a non-transitory computer readable medium storing executable instructions. The executable instructions include a layer segmentation component is configured to identify and segment a plurality of retinal layers within the set of OCT data. The plurality of layers include a layer of interest. A mapping component is configured to generate at least one of an en face representation of the layer of interest and a three-dimensional reconstruction of the layer of interest from the segmented plurality of layers. A parameter generator is configured to derive at least one parameter, representing a thickness of the layer of interest, from at least one of the en face representations of the layer of interest and the three-dimensional reconstruction of the layer of interest. A user interface is configured to provide the determined at least one parameter to a display.

In accordance with another aspect of the present invention, a method is provided for evaluating an eye of a patient from a set of OCT data. A plurality of retinal layers within the set of OCT data are segmented via an automated process. The plurality of layers include a layer of interest. At least one of an en face representation of the layer of interest and a three-dimensional reconstruction of the layer of interest is generated from the segmented plurality of layers. At least one parameter representing a thickness of the layer of interest is derived from the at least one of the en face representation of the layer of interest and the three-dimensional reconstruction of the layer of interest. The determined at least one parameter is provided to a user at a display.

In accordance with yet another aspect of the present invention, a system is provided for evaluating an eye of a patient from a set of OCT data. The system includes a processor and a non-transitory computer readable medium storing executable instructions. The executable instructions include a layer segmentation component configured to identify and segment a plurality of retinal layers within the set of OCT data. The plurality of layers include a layer of interest. A mapping component is configured to generate at least one of an en face representation of the layer of interest and a three-dimensional reconstruction of the layer of interest from the segmented plurality of layers. A parameter generator includes a feature extractor configured to extract at least one numerical feature representing a thickness of the layer of interest from the at least one of the en face representation of the layer of interest and the three-dimensional reconstruction of the layer of interest and a classifier configured to assign one of a categorical class and a numerical parameter to the patient from the at least one numerical feature. The parameter represents one of a clinical prognosis and a diagnosis of a given disorder. A user interface is configured to provide the assigned at least one parameter to a display.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The outer retina is characterized by four highly reflective bands can be seen in outer retina in SDOCT images in normal eye, the external limiting membrane (ELM), the ellipsoid zone (EZ), the interdigitation zone (IZ, or cone outer segment tips) and the retinal pigment epithelium (RPE). Additionally, the outer retina includes the photoreceptor nuclei in the outer nuclear layer (ONL), a hyporeflective band anterior to the outer hyperreflective bands. For the purpose of this application, the outer retina is defined as the portion of the retina bounded by the outer plexiform layer and the retinal pigment epithelium, and an outer retinal layer is any distinct layer in this region, such as the ONL, ELM, EZ, IZ, and RPE. The inventors utilize these layers and other layers in the outer retina to evaluate visual outcomes and prognosis in macular diseases, track the progression of therapeutic interventions, and diagnosis other disorders, for example, disorders of the central nervous system. Systems and methods in accordance with the present invention provide visual and quantitative assessment across an OCT data set.

Figure 1:
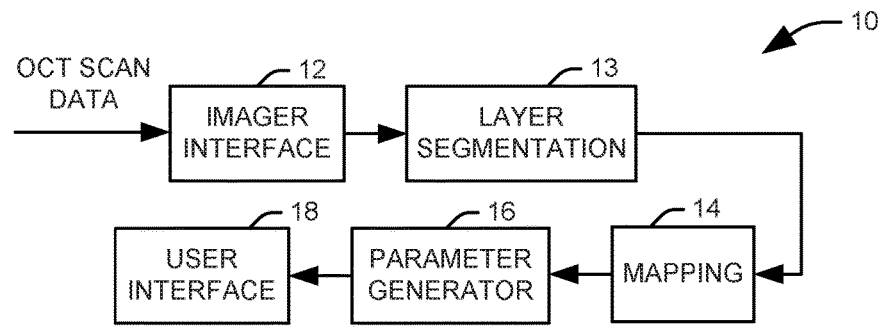
FIG. 1 illustrates a functional block diagram of a system for evaluating an eye of a patient from a OCT scan in accordance with an aspect of the present invention.

FIG. 1 illustrates a functional block diagram of a system 10 for evaluating an eye of a patient from an OCT scan in accordance with an aspect of the present invention. It will be appreciated that the system 10 can be implemented as dedicated hardware, machine executable instructions stored on a non-transitory computer readable medium and executed by an associated processor, referred to herein as software, or some combination of dedicated hardware and software components. It will be appreciated that the system 10 can be implemented as a standalone system working in conjunction with an OCT scanner or as an integral part of an OCT scanner.

The system 10 includes an imager interface 12 configured to receive OCT scan data from an associated scanning assembly. In one implementation, the OCT data can include spatial domain optical coherence technology (SDOCT) data. The images are provided to a layer segmentation component 13 configured to determine identify and segment a plurality of retinal layers. For example, the layer segmentation component 13 can identify specific retinal layers and truncate the image to include only those layers within the image. In one implementation, the layer segmentation component 13 is provided with the macular cube for analysis, and the retinal layers include either or both of the ellipsoid zone and the outer nuclear layer.

The segmented layers can be provided to a mapping component 14 configured to extract parameters and graphical representations of the layer of interest and surrounding retinal layers. For example, the mapping component 14 can generate an en face view of the layer of interest as well as a volumetric reconstruction of the layer of interest and surrounding retinal layers. A parameter generator 16 can derive at least one parameter, representing a thickness of the layer of interest, from the graphic representation of the layer of interest. In one example, one more features can be derived directly from measurements taken from the en face representation and the volumetric reconstruction of the layer of interest. For example, a numerical feature can include any of the following: a percentage of the layer of interest having at least a specified height (e.g., 20 microns, 10 microns, 0 microns), a volume of the layer of interest, or a percentage of the area of the scan for which the layer of interest is absent. In another example, one or more features can be derived longitudinally, such that the numerical feature represent a difference in a given measurement between a current mapping of the layer of interest and surrounding layers and a past mapping of the layer of interest.

In still another example, the parameter generator 16 is configured to extract one or more parameters based on spatial patterns of pathologies or other clinically relevant events. For example, subclinical hydroxychloroquine toxicity can present as an attenuation of ellipsoid zone in a series of concentric circles, and the parameter generator 16 can compute a similarity of a pattern of attenuation, if any, in an imaged eye to a sample pattern, with the similarly value used as a feature. Finally, the parameter generator 16 can include a supervised learning algorithm, such as a classification or regression model, to assign either a categorical parameter (i.e., a class) or a continuous parameter to the patient based on other measurements of the mapped layer of interest. For example, a continuous parameter can represent a likelihood that a patient will respond to a given treatment or that a patient has a given disorder or the severity of a given disorder. Example classes can include diagnosis classes (e.g., a normal class and one or more disorder classes) or prognosis classes associated with a therapeutic intervention. It will be appreciated that additional features, such as biometric parameters (age, sex, intraocular pressure, etc.) and a medical history of the patient, can also be used in the classification. The supervised learning algorithm can include, for example, any of rule-based classifiers, regression models, neural networks, and statistical classifiers.

The generated parameters are displayed to a user at a user interface 18. In one example, the en face representation and volumetric reconstruction of the layer of interest can be provided to the user as well, with appropriate tools for viewing and manipulating the reconstructed layer and surrounding layers. In one implementation, this can include a binary view of the layer of interest, showing the presence or absent of the layer of interest within the scanned region, a gradient view, or a heat map representation of the thickness of the layer of interest.

Figure 2:
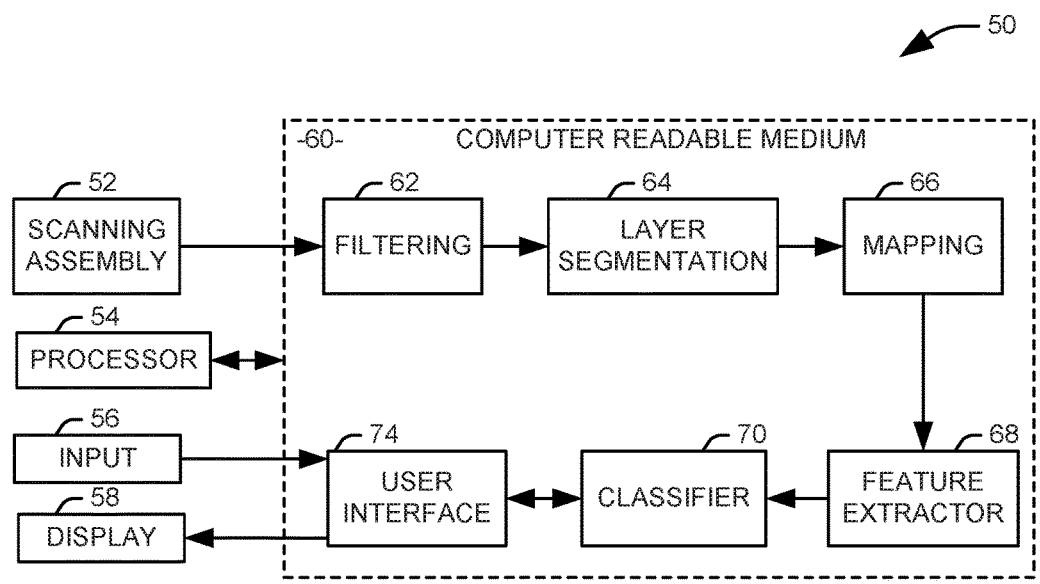
FIG. 2 illustrates one implementation of a system for evaluating a condition of an eye of a patient from a series of OCT B-scans in accordance with an aspect of the present invention.

FIG. 2 illustrates one implementation of a system 50 for evaluating a condition of an eye from a series of OCT B-scans in accordance with an aspect of the present invention. An OCT scanning assembly 52 provides OCT B-scan data suitable for volumetric reconstruction to an image analysis component implemented as a general purpose processor 54 operatively connected to a non-transitory computer readable medium 60 storing machine executable instructions. An input device 56, such as a mouse or a keyboard, is provided to allow a user to interact with the system, and a display 58 is provided to display imaging data and calculated parameters to the user.

The machine executable instructions include a filtering component 62 that conditions the received B-scan images for further analysis. In one implementation, image smoothing is performed at the filtering component using a Gaussian convolution window to attenuate noise. A layer segmentation component 64 performs an automated delineation of a set of retinal layer boundaries for each image. In the illustrated implementation, layer boundaries are delineated by local image intensity, gradient, and contrast cues that are determined from immediate pixel neighbors and local regional properties. An optimal segmentation of boundaries is performed via a sparse maximum-flow minimum-cut graph search on a planar, four-connected graph representation of the weighted contributions of pixel intensity, pixel gradient, and/or shape/location cues from adjacent frames on a multi-frame image stack. The result of the maximum-flow minimum-cut analysis identifies the globally optimal boundary with greatest image intensity or image gradient. For example, the natural topological constraints in retinal/posterior segment images can be the boundaries of the external limiting membrane and the retinal pigment epithelium (RPE).

The constraint boundary determination at the layer segmentation component 64 is performed with pixel-level accuracy. This allows the option of using the identified layer boundaries for a determination of width, height, thickness, area, volume, or other geometry of the retinal layers. The layer segmentation component 64 also allows a user to provide an operator-assisted determination of constraint boundaries via the input device 56 in the event of an automated boundary detection failure or if it is desirable to select specific pathologic structures of interest. Once the layer boundaries are determined, the layer segmentation component 64 truncates the image to remove the image area outside of the segmented layers, decreasing the computation time of any further segmentation or processing.

A mapping component 66 is configured to provide a three-dimensional reconstruction of at least the layer of interest from the segmented layers. In the illustrated implementation, the mapping component can produce volumetric representations of the layer of interest and a set of layers surrounding layers. As part of this process, regions of cross-sectional area and cubic volumetric data are generated related to layer of interest, and three-dimensional reconstruction was also performed with embedded mapping for visualization of areas of pathology. Finally, en face thickness topographic maps of the layer of interest were created for each scan.

A feature extractor 68 is configured to extract a plurality of numerical features from the reconstruction of the layer of interest. These features can include a plurality of volumetric, area, and linear parameters. The specific volumetric parameters to be calculated can vary with the application and can include, for example, a total volume, an area, a maximal thickness, and a minimum thickness of the layer of interest. To evaluate attenuation within the layer of interest and surrounding layers, the feature extractor 68 can calculate a percentage of the layer of interest that has a thickness less than a threshold value, such as twenty microns, on the en face mapping. Similarly, a percentage of the layer of interest that is completely absent can be determined. Patterns of attenuation, that is, regions of the layer of interest having a thickness below a threshold, can also be distinguished, for example, via template matching process in which a similarity measure is determined between the attenuation pattern and one or more exemplars representing known attenuation patterns associated with various disorders. Finally, longitudinal parameters for any of these features can be determined using the results of previous segmentations to determine a change in the layer of interest over time.

The extracted features can also be provided to a classifier 70 configured to evaluate either a clinical outcome or a diagnosis for a patient according to at least the calculated features. Specifically, the classifier 70 either produces a numerical parameter representing the clinical outcome or diagnosis, for example, as a likelihood, or assigns a class to the patient representing the outcome or diagnosis. It will be appreciated, of course, that the classifier may also use other predictors associated with the patient, including categorical predictors, such as predictors representing medical history and the presence or absence of various conditions, as well as integral or ratio parameters, such as age, blood glucose level, or similar parameters. The classifier 70 can include one or more appropriate supervised learning algorithms, such as regression models, artificial neural networks, support vector machines, and statistical classifiers that predict or diagnose a clinical outcome using the calculated features as predictors in the model.

In one example, the classifier 70 can be used to provide decision support for a physician in conducting a therapeutic intervention by recommending one or more parameters for the intervention itself or for post-intervention care. Alternatively, the classifier 70 can evaluate patients according to the likelihood that a given patient will respond to a given intervention, or the likelihood that a previous intervention will result in improved visual acuity from longitudinal parameters drawn from pre-invention and post-invention scans. The results of the classification can be provided to a user interface 74 for display to the user.

The inventors have determined that patients with age related macular degeneration (AMD) and geographic atrophy exhibit multi-focal areas of EZ loss on the en face map and decreased EZ-RPE volume relative to normal eyes. Patients with mild hydroxychloroquine toxicity exhibit a concentric thinning of the EZ-RPE thickness with associated foveal sparing. Patients with Stargardt disease exhibit a decrease in EZ volume, EZ attenuation, and EZ atrophy relative to normal eyes. Accordingly, features that might be used in distinguishing among these disorders and a normal eye could include the EZ volume, a percentage of the EZ area that is atrophied (zero thickness), and a percentage of the EZ area in which the EZ-RPE thickness is less than twenty microns, as well as a pattern-based feature for identifying the concentric thinning pattern associated with hydroxychloroquine toxicity. Specific patterns may be present in numerous diseases including but not limited to macular degenerative disease, macular dystrophies, drug toxicities, inherited retinal degenerations, diabetic retinopathy, and inflammatory eye disease In another example, the efficacy of treatment of symptomatic vitreomacular traction (VMT) with injections of ocriplasmin can be evaluated using the system 50. The inventors have determined that successful treatments, that is treatments in which VMT release was achieved, showed dramatic reductions in the EZ area and volume at one week after the treatment relative to patients who did not respond to the treatment. This reduction recovered over time to the baseline value. Accordingly, changes in the area and volume of the EZ area one week after treatment can be utilized as a feature to predict or diagnose the response of the patient to the ocriplasimin injection.

In still another example, thinning of the outer nuclear layer has been found to be an early symptom of disorders of the central nervous system. Features that might be used in screening for these disorders and a normal eye could include the outer nuclear layer volume, a percentage of the scan area for which the outer nuclear layer is atrophied (zero thickness), and a percentage of the scan area in which the outer nuclear layer thickness is less than a threshold thickness.

Figure 3:
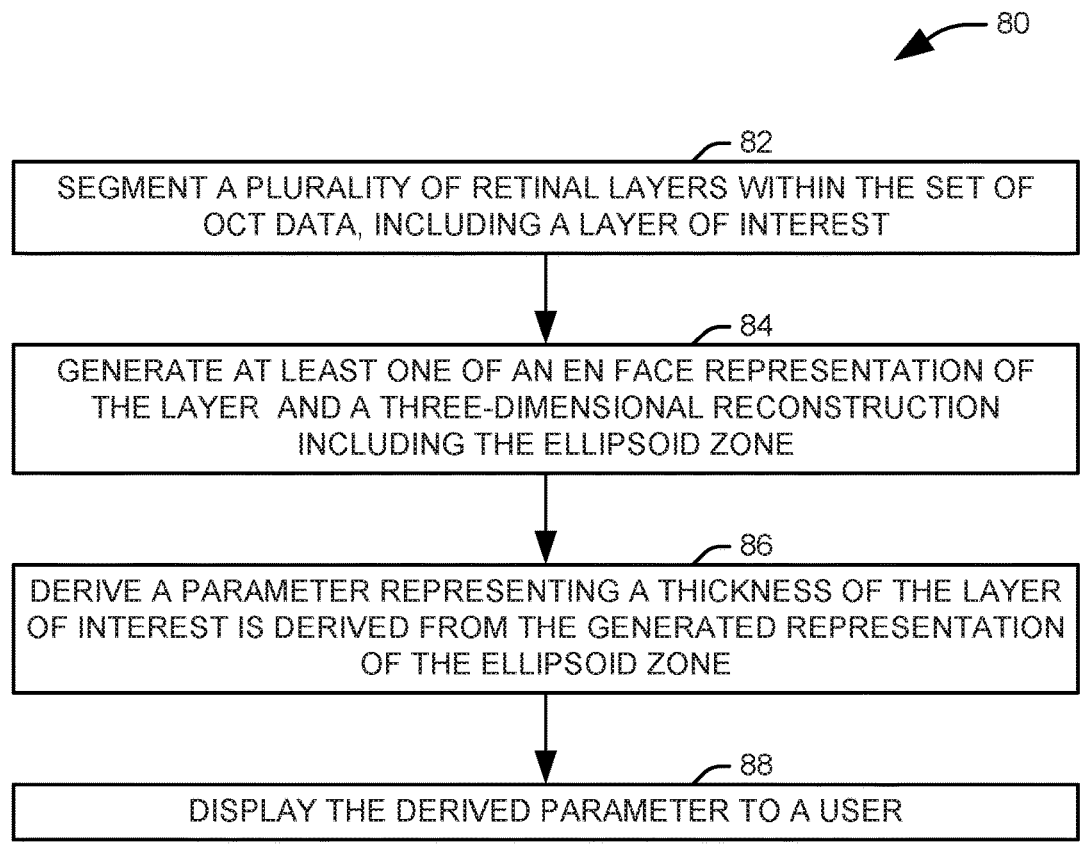
FIG. 3 illustrates a method for evaluating a condition of an eye of a patient in accordance with an aspect of the present invention.
Figure 4:
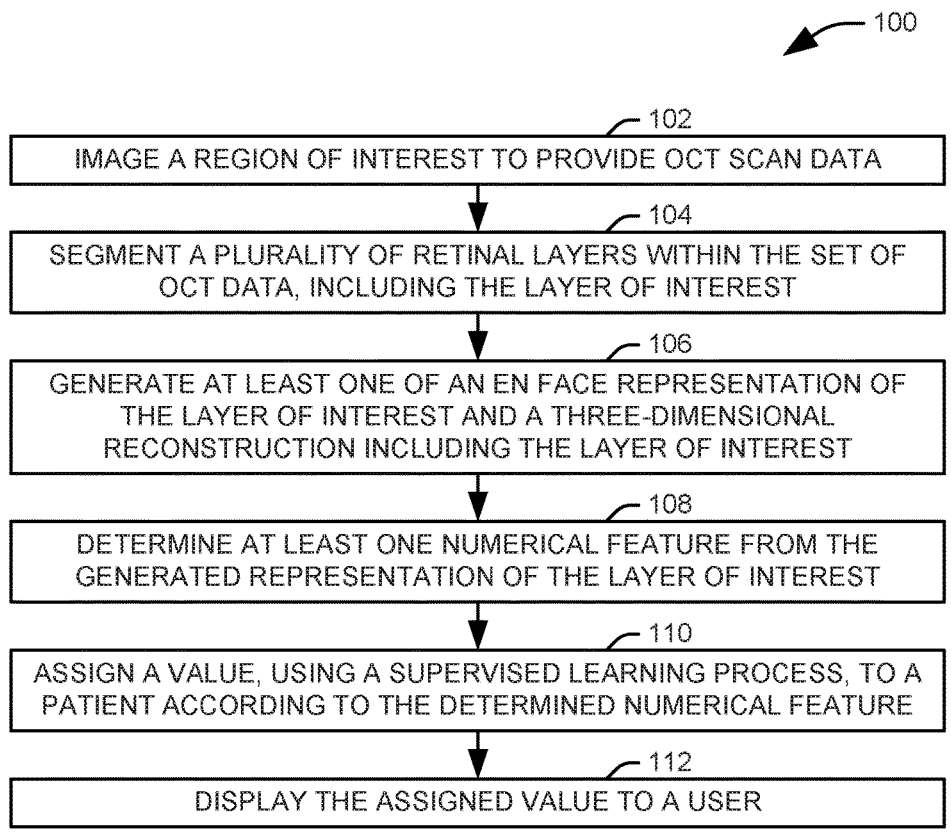
FIG. 4 illustrates a method for classifying an eye of a patient in accordance with an aspect of the present invention.

In view of the foregoing structural and functional features described above, a method in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 3 illustrates a method 80 for evaluating an eye of a patient from a set of OCT data. At 82, a plurality of retinal layers within the set of OCT data are segmented via an automated process. In one implementation, the set of OCT data is spatial domain OCT data taken according to a macular cube protocol, but it will be appreciated that any data suitable for volumetric reconstruction of a portion of the retina can be used. The plurality of layers include a layer of interest. In one implementation, the layer of interest is an outer retinal layer. At 84, at least one of an en face representation of the layer of interest and a three-dimensional reconstruction of the layer of interest is generated from the segmented plurality of layers.

At 86, at least one parameter representing a thickness of the layer of interest is derived from the at least one of the en face representation of the layer of interest and the three-dimensional reconstruction of the layer of interest. Example parameters can include a percentage of the layer of interest having a thickness less than a threshold value, a volume of the layer of interest, and a similarity of an attenuation pattern of the layer of interest to a known pattern associated with a retinal disorder. At 88, the determined at least one parameter is provided to a user at a display. In one implementation, each of the en face representation of the layer of interest and a three-dimensional reconstruction of the layer of interest are generated and retained for display to a user.

FIG. 4 illustrates a method 100 for classifying an eye of a patient in accordance with an aspect of the present invention. At 102, a region of interest containing a layer of interest is imaged to provide a set of pre-intervention scan data. In one implementation, the imaging is performed on a region of eye tissue according to the macular cube protocol using an OCT imager to provide a series of B-scan images. At 104, an automated process is applied to segment a plurality of retinal layers within the set of OCT data that includes the layer of interest. At 106, at least one of an en face representation of the layer of interest and a three-dimensional reconstruction of the layer of interest from the segmented plurality of layers. During this process, each of volumetric, linear, and area parameters for the layer of interest can be determined.

At 108, at least one numerical feature is determined from the at least one of the en face representation of the layer of interest and the three-dimensional reconstruction of the layer of interest. Numerical features can represent, for example, any of a thickness, area, or volume of the layer of interest, a change in one of these values from a previous scan, a percentage of the area of the layer of interest falling below a threshold thickness, or a similarly of a determined attenuation pattern to a known template. In one implementation, numerical features can be extracted from an ellipsoid zone of the retina to diagnose or track the progression of retinal disorders such as age-related macular degeneration (AMD), hydroxychloroquine toxicity, diabetic retinopathy. In another implementation, numerical features can be extracted from an outer nuclear layer of the retina to diagnose disorders of the central nervous system.

At 110, a value is assigned to the patient representing one of a clinical prognosis and a diagnosis of a given disorder from the at least one numerical feature. For example, the numerical features can be provided to one or more supervised learning algorithms to provide a categorical or numerical value representing the diagnosis or prognosis. At 112, the assigned value is displayed to a user at an associated output device.

Figure 5:
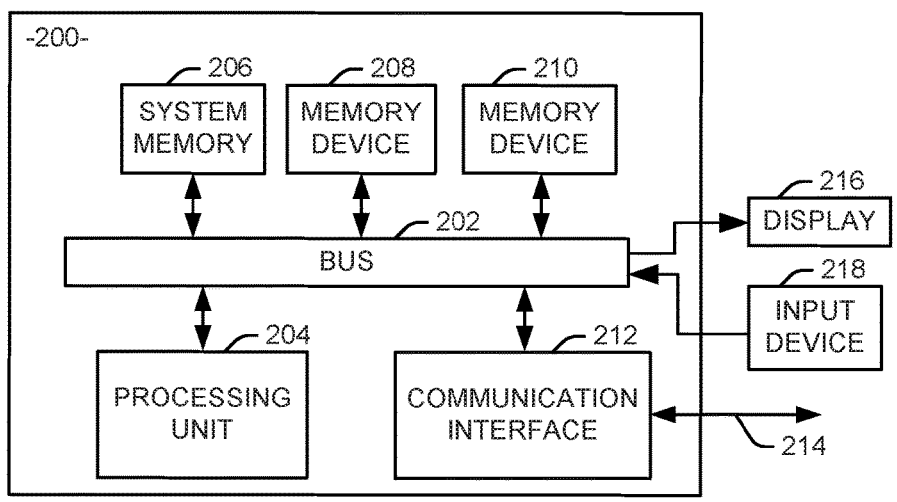
FIG. 5 is a schematic block diagram illustrating an exemplary system of hardware components capable of implementing examples of the systems and methods disclosed herein.

FIG. 5 is a schematic block diagram illustrating an exemplary system 200 of hardware components capable of implementing examples of the systems and methods disclosed in FIGS. 1-4, such as the imaging systems illustrated in FIGS. 1 and 2. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an OCT imaging system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

From the above description of the invention, those skilled in the art will perceive improvements, changes, and modifications. Such improvements, changes, and modifications within the skill of the art are intended to be covered by the appended claims.

Having described the invention, we claim:

1. A system for evaluating an eye of a patient from a set of OCT data comprising:
    a processor; and
    a non-transitory computer readable medium storing executable instructions comprising:
        a layer segmentation component that identifies and segments a plurality of retinal layers within the set of OCT data, the plurality of layers comprising a layer of interest, wherein the layer of interest is an outer retinal layer;
        a mapping component that generates at least one of an en face representation of the layer of interest and a three-dimensional reconstruction of the layer of interest from the segmented plurality of layers;
        a parameter generator that derives at least one parameter, representing a thickness of the layer of interest, from the at least one of the en face representation of the layer of interest and the three-dimensional reconstruction of the layer of interest, the at least one parameter comprising one of a volume of the layer of interest, a percentage of the layer of interest having a thickness less than a threshold value, a similarity measure between an attenuation pattern present in the layer of interest and a known pattern associated with a disorder, a percentage of the layer of interest that has atrophied, with a thickness in an atrophied location being zero, and a change in one of these parameters over time; and a user interface that provides the determined at least one parameter to a display.

2. The system of claim 1, wherein the layer of interest is one of an ellipsoid zone, interdigitation zone, external limiting membrane, and an outer nuclear layer of the retina.

3. The system of claim 1, the parameter generator comprising:
a feature extractor configured to extract at least one numerical feature representing the thickness of the layer of interest from the at least one of the en face representation of the layer of interest and the three-dimensional reconstruction of the layer of interest; and
a classifier configured to assign the at least one parameter, comprising one of a categorical class and a numerical parameter and representing one of a clinical prognosis and a diagnosis of a given disorder, to the patient from the at least one numerical feature.

4. The system of claim 1, the at least one parameter comprising the percentage of the layer of interest having a thickness less than a threshold value.

5. The system of claim 1, the at least one parameter comprising the percentage of the layer of interest that has atrophied.

6. The system of claim 1, the at least one parameter comprising the volume of the layer of interest.

7. The system of claim 1, the at least one parameter comprising the similarity measure between the attenuation pattern present in the layer of interest and the known pattern.

8. The system of claim 1, the parameter generator being configured to generate a difference of one of a first volume of the layer of interest, a first thickness of the layer of interest in a specific location, and a first percentage of layer of interest having a thickness less than a threshold value determined from the set of OCT scan data and a corresponding one of a second volume of the layer of interest, a second thickness of the layer of interest in a specific location, and a second percentage of layer of interest having a thickness less than a threshold value determined from a previous set of OCT scan data.

9. The system of claim 1, the mapping component generating both of the en face representation of the layer of interest and the three-dimensional reconstruction of the layer of interest from the segmented plurality of layers.

10. A method for evaluating an eye of a patient from a set of OCT data comprising:
segmenting, via an automated process, a plurality of retinal layers within the set of OCT data, the plurality of layers comprising a layer of interest, wherein the layer of interest is an outer retinal layer;
generating at least one of an en face representation of the layer of interest and a three-dimensional reconstruction of the layer of interest from the segmented plurality of layers;
deriving at least one parameter representing a thickness of the layer of interest from the at least one of the en face representation of the layer of interest and the three-dimensional reconstruction of the layer of interest, the at least one parameter comprising one of a volume of the layer of interest, a percentage of the layer of interest having a thickness less than a threshold value, a similarity measure between an attenuation pattern present in the layer of interest and a known pattern associated with a disorder, a percentage of the layer of interest that has atrophied, with a thickness in an atrophied location being zero, and a change in one of these parameters over time; and
providing the determined at least one parameter to a user at a display.

11. The method of claim 10, wherein deriving the at least one parameter representing the thickness of the layer of interest comprises:
extracting at least one numerical feature representing the thickness of the layer of interest from the at least one of the en face representation of the layer of interest and the three-dimensional reconstruction of the layer of interest; and
assigning the at least one parameter, comprising one of a categorical class and a numerical parameter and representing one of a clinical prognosis and a diagnosis of a given disorder, to the patient from the at least one numerical feature.

12. The method of claim 10, wherein deriving the at least one parameter representing the thickness of the layer of interest comprises generating a percentage of layer of interest having a thickness less than a threshold value.

13. The method of claim 10, wherein deriving the at least one parameter representing the thickness of the layer of interest comprises generating a similarity measure between an attenuation pattern present in the layer of interest and a known pattern associated with a disorder.

14. The method of claim 10, further comprising obtaining the set of OCT data according to a macular cube protocol at an associated OCT scanner.

15. The method of claim 10, further comprising obtaining the set of OCT data as a set of spectral domain OCT data.

16. A system for evaluating an eye of a patient from a set of OCT data comprising:
a processor; and
a non-transitory computer readable medium storing executable instructions comprising:
a layer segmentation component configured to identify and segment a plurality of retinal layers within the set of OCT data, the plurality of layers comprising a layer of interest;
a mapping component configured to generate at least one of an en face representation of the layer of interest and a three-dimensional reconstruction of the layer of interest from the segmented plurality of layers;
a parameter generator comprising:
a feature extractor configured to extract at least one numerical feature representing a thickness of the layer of interest from the at least one of the en face representation of the layer of interest and the three-dimensional reconstruction of the layer of interest; and
a classifier configured to assign at least one parameter, comprising one of a categorical class and a numerical parameter and representing one of a clinical prognosis and a diagnosis of a given disorder, to the patient from the at least one numerical feature; and a user interface configured to provide the assigned at least one parameter to a display.

17. The system of claim 16, wherein the layer of interest is an outer nuclear layer of the retina and the at least one parameter represents the presence or absence of a disorder of the central nervous system.

18. The system of claim 17, wherein the layer of interest is an ellipsoid zone of the retina and the at least one parameter represents the presence or absence of a disorder of the central nervous system.

* * * * *